(12) United States Patent
Zhong et al.

(10) Patent No.: US 10,361,587 B2
(45) Date of Patent: Jul. 23, 2019

(54) WIRELESS SENSOR

(71) Applicant: The University of Bristol, Bristol (GB)

(72) Inventors: ChengHuan Zhong, Bristol (GB); Anthony Croxford, Bristol (GB); Paul Wilcox, Bristol (GB)

(73) Assignee: THE UNIVERSITY OF BRISTOL, Bristol (GB)

( * ) Notice: Subject to any disclaimer, the term of this patent is extended or adjusted under 35 U.S.C. 154(b) by 0 days.

(21) Appl. No.: 15/326,009

(22) PCT Filed: Jun. 30, 2015

(86) PCT No.: PCT/GB2015/051912
§ 371 (c)(1),
(2) Date: Jan. 12, 2017

(87) PCT Pub. No.: WO2016/009174
PCT Pub. Date: Jan. 21, 2016

(65) Prior Publication Data
US 2017/0214274 A1    Jul. 27, 2017

(30) Foreign Application Priority Data

Jul. 15, 2014   (GB) .................................. 1412572.8

(51) Int. Cl.
*H02J 50/10*        (2016.01)
*G01N 29/24*        (2006.01)
(Continued)

(52) U.S. Cl.
CPC .............. *H02J 50/10* (2016.02); *G01D 11/30* (2013.01); *G01N 29/2475* (2013.01);
(Continued)

(58) Field of Classification Search
CPC ................................. H02J 50/10; G01D 11/30
See application file for complete search history.

(56) References Cited

U.S. PATENT DOCUMENTS 6,939,299 B1 *   9/2005   Petersen .................. A61B 3/16
                                                        600/300
9,713,429 B2 *   7/2017   Schmidt ................. A61B 5/031
(Continued)

FOREIGN PATENT DOCUMENTS

CN          103148977 A      6/2013
JP          2004129185 A     4/2004
(Continued)

OTHER PUBLICATIONS

Young, Darrin J., et al. "Wireless power recharging for implantable bladder pressure chronic monitoring." Nano/Micro Engineered and Molecular Systems (NEMS), 2010 5th IEEE International Conference on. IEEE, 2010.*
(Continued)

*Primary Examiner* — Daniel J Cavallari
(74) *Attorney, Agent, or Firm* — One LLP; Jonathan Jaech

(57) ABSTRACT

This application relates to a wireless sensor (10) suitable for non-destructive testing of a test object. The sensor comprises a transducer (12) and an electrically conductive transducer coil (16) configured to define an enclosure and being electrically coupled to the transducer to enable the transducer to be inductively operated by a remote device. The enclosure defined by the transducer coil has an internal width dimension that is wider than a corresponding width dimension of the transducer.

18 Claims, 3 Drawing Sheets

(51) Int. Cl.
*H02J 50/90* (2016.01)
*H01F 38/14* (2006.01)
*H01F 27/28* (2006.01)
*G01D 11/30* (2006.01)

(52) U.S. Cl.
CPC ..... *G01N 29/2481* (2013.01); *H01F 27/2804* (2013.01); *H01F 27/2823* (2013.01); *H01F 27/2885* (2013.01); *H01F 38/14* (2013.01); *H02J 50/90* (2016.02)

(56) References Cited

U.S. PATENT DOCUMENTS

| | | | |
|---|---|---|---|
| 2003/0105394 | A1 | 6/2003 | Fabian et al. |
| 2003/0109175 | A1* | 6/2003 | Skinner .............. H01R 13/6596 439/607.01 |
| 2008/0281212 | A1 | 11/2008 | Nunez et al. |
| 2011/0101788 | A1* | 5/2011 | Sun ........................ H01F 38/14 307/104 |
| 2011/0287713 | A1 | 11/2011 | ALi et al. |
| 2012/0007579 | A1 | 1/2012 | Apblett et al. |
| 2012/0240681 | A1* | 9/2012 | Lopez Jauregui ... G01N 29/043 73/643 |
| 2014/0102198 | A1 | 4/2014 | Froster |
| 2016/0077843 | A1* | 3/2016 | Jakoboski ............... G06F 1/266 710/8 |

FOREIGN PATENT DOCUMENTS

| | | | |
|---|---|---|---|
| JP | 2005078473 A1 | | 3/2005 |
| JP | 2005-228785 A | | 8/2005 |
| JP | 2006-024087 A | | 1/2006 |
| JP | 2007125104 A | | 5/2007 |
| JP | 2011-066627 A | | 3/2011 |
| KR | 101385697 B1 | * | 4/2014 |
| WO | 2003106952 A2 | | 12/2003 |
| WO | 2012085333 A1 | | 6/2012 |
| WO | 2013003754 A1 | | 1/2013 |
| WO | 2016009174 A1 | | 1/2016 |

OTHER PUBLICATIONS

Oct. 25, 2009, Peng Cong et al., "Wireless Power recharging for Implantable Bladder Pressure Sensor", pp. 1670-1673.
Feb. 1, 2014, Luo Mengdi et al., "A Microfabricated Wireless RF Pressure Sensor Made Completely of Biodegradable Materials", Journal of Microelectromechanical Systems, pp. 4-13.
PCT International Search Report dated Sep. 18, 2015 for PCT/GB2015/051912.
Search Report dated Jan. 15, 2015 for related Great Britain application No. GB1412572.8.
Examination Report Under Section 18(3) dated Oct. 9, 2015 for related Great Britain application No. GB1412572.8.
Combined Search and Examination Report Under Section 17 and 18(3) dated May 15, 2015 for related Great Britain application No. GB1412572.8.
Examination Report Under Section 18(3) dated May 31, 2016 for related Great Britain application No. GB1412572.8.
Greve, D.W., et al., "An Inductively Coupled (Wireless) Lamb Wave Transducer", Carnegie Mellon University, Pittsburgh, PA, from https://pdfs.semanticscholar.org/5sec2/f51df0ce0b0d1edbc7c6e9245094ecf4c618.pdf on May 18, 2018, pp. 1-7.
Kobayashi, M., et al., "Structural Health Monitoring of Composites Using Integrated and Flexible Piezoelectric Ultrasonic Transducers", Journal of Intelligent Material Systems and Structures, vol. 20, 2009, pp. 969-977.
Murayama, R., et al., "Noncontact Driving System Using Induction-Based Method and Integrated Piezoelectric Ultrasonic Transducers", Journal of Sensor Technology, vol. 2, 2012, pp. 60-67.
Sun, Z., et al., "A Methodological Review of Piezoelectric Based Acoustic Wave Generation and Detection Techniques for Structural Health Monitoring", International Journal of Aerospace Engineering, 2013, pp. 1-22.
Japanese Patent Application No. 2016-571726 Office Action dated May 7, 2019.
European Patent Application No. 15736018.1 Summons to Oral Proceedings dated May 6, 2019.

* cited by examiner

WIRELESS SENSOR

CROSS REFERENCE TO RELATED APPLICATIONS

This application claims priority to Great Britain application Ser. No. 1412572.8 filed Jul. 15, 2014 and to International (PCT) Application Number PCT/GB2015/051912 filed Jun. 30, 2015, which applications are hereby incorporated by reference in their entireties.

BACKGROUND

Non-destructive testing (NDT) is used extensively across a range of industries to evaluate the properties of a test object without causing damage to the test object. Examples of test objects include composite aircraft panels, gas-turbine engine components, pipelines and pressure vessels.

It is known to integrate an NDT sensor into a test object in order to provide, for example, reliable repeatable measurement and/or in situ monitoring while the test object is in service. For example, it is known to integrate an ultrasonic sensor in or on a test object.

Performing measurements using an integrated NDT sensor can however be challenging due to the difficulty associated with making wired connections to an integrated NDT sensor. One option for addressing this problem is to provide an integrated NDT sensor with its own power storage device, but this can result in a bulky sensor. Moreover, recharging or replacing the power storage device can be difficult if the integrated sensor is inaccessible; for example, if the sensor is partially or fully embedded within the test object.

It is therefore known to provide wireless integrated NDT sensors that can be inductively coupled to an external measurement device. The inductive coupling enables power to be provided to the integrated sensor from the external device in a similar manner to known radio-frequency identification (RFID) modules. The inductive coupling can also be used for the transfer of measurement information from the integrated sensor back to the external device.

However, the present inventors have identified that known wireless NDT sensors can be large, heavy and/or overly complex in design.

SUMMARY OF INVENTION

According to a first aspect of the present invention there is provided a wireless sensor suitable for non-destructive testing of a test object, the sensor comprising:
a transducer arranged to non-destructively test a property of the test object; and
an electrically conductive transducer coil configured to define an enclosure and being electrically coupled to the transducer to enable the transducer to be inductively operated by a remote device,
wherein the enclosure defined by the transducer coil has an internal width dimension that is wider than a corresponding width dimension of the transducer.

The transducer may comprise an electrically conductive element; for example, an electrode. When a wireless sensor is powered inductively, the transmitting coil of the external measurement device can generate eddy currents in a conductive electrode of the transducer. These in turn generate a magnetic field that destructively interacts with the incident field from the transmitting coil, which acts to decouple the transducer coil from the source field, thereby defining a 'decoupled space' directly above the transducer. The transducer coil according to the first aspect of the invention defines an enclosure that is sized such that some or all of the coil is outside of the decoupled space, thereby avoiding the need for a protective ferrite core or the like to be provided to refine the magnetic field. This enables a lighter, more compact sensor to be provided, which is especially advantageous in embedded sensor applications; for example, when embedding a sensor in a carbon fibre composite test object, such as an aircraft part, it is important for the sensor to be low profile i.e. thin in the direction perpendicular to the width direction in order to minimise the impact on structural integrity.

The enclosure defined by the transducer coil can have a plurality of distinct internal width dimensions each of which is wider than a corresponding width dimension of the transducer. This can enable a sensor arrangement with a small footprint i.e. width, and can enable an improved inductive coupling between the sensor and external measurement device in comparison to an embodiment in which the transducer coil has a single internal width dimension that is wider than a corresponding width dimension of the transducer.

The enclosure defined by the transducer coil can be sized to receive the transducer. This can enable a low profile sensor arrangement, and in some embodiments can enable the transducer coil to surround the uncoupled space.

The transducer coil can be mounted in the same plane as the transducer, with the transducer located within the enclosure defined by the transducer coil. This can result in an optimum low profile sensor arrangement.

The transducer coil can be mounted relative to the transducer in a generally coaxial, parallel relationship in which the transducer coil is spaced from the transducer by no more than five times the thickness of the transducer, preferably by no more than three times and even more preferably by no more than twice the thickness of the transducer. The thickness may refer to the average thickness, or the greatest thickness of the transducer. In some embodiments the transducer coil is spaced from the transducer by no more than 6 mm, preferably no more than 4 mm, preferably no more than 3 mm and even more preferably no more than 2 mm or 1 mm. Such embodiments can enable dynamic separation between the coil and sensor but still with good sensor localisation as the sensor is right below the coil, which can be advantageous in embedded sensor applications.

The coil can have one or more distinct inner width dimensions each of which is at least 1.1 times the corresponding outer width dimension of the transducer. This can provide a buffer space between the coil and the uncoupled space or the transducer. In embodiments where the coil is sized to receive the transducer, this can simplify the provision of electrical couplings to the transducer. In embodiments where the transducer gives rise to an uncoupled space, the increased separation between the uncoupled space and coil can reduce the effect of the uncoupled space on the inductive coupling between the transmitting coil and transducer coil.

One or more distinct inner width dimensions can each be between 1.01 and 10 times the corresponding outer width dimension of the transducer, preferably between 1.01 and 5 times, more preferably between 1.01 and 2 times, more preferably between 1.01 and 1.5 times and even more preferably between 1.01 and 1.1 times the corresponding outer width dimension of the transducer. Such embodiments can provide an optimum trade-off between buffer space between the coil and the uncoupled space or transducer on the one hand and overall sensor width on the other hand.

An inner width dimension of the coil can be a diameter and the corresponding outer width dimension of the transducer can be a diameter. A disc shaped transducer can provide omni-directional measurement sensitivity in guided wave applications, for good coverage.

The sensor can include a layer of electromagnetic interference (EMI) absorber provided between the transducer coil and a coupling face of the sensor, the coupling face being arranged to be coupled to the test object. In use, the coupling face can be on an opposite side of the sensor with respect to the transmitter coil. When the transmitting coil is placed in proximity to a metallic structure, eddy currents are induced on the surface of the structure. Due to the magnetic field caused by the eddy currents, the coupling between the transmitting and transducer coils is reduced, particularly when the transducer coil is placed directly on the surface of a metallic structure. The EMI absorber absorbs incident electromagnetic radiation from the transmitting coil, and thus can eliminate the eddy currents in the metallic structure, enabling the sensor to be mounted on a surface of a metallic structure.

The layer of EMI absorber can be thinner than the transducer, and in some cases can be thinner than the difference in thickness between the transducer and coil. This can provide a compact, low profile sensor that can be used with metallic structures.

The EMI absorber and/or the transducer coil and/or the transducer can be formed from a flexible material. This can enable the sensor to be applied to curved structures.

The transducer can comprise one of: a thermal transducer; an ultrasound transducer; a strain gauge; a chemical sensor; and accelerometer; and an electromagnetic transducer.

The coil can be arranged as a planar coil, and in some cases formed on a single or double sided PCB.

In accordance with a second aspect of the present invention, there is provided a test object including one or more sensors according to the first aspect coupled to it.

The test object can comprise a composite component, such as a composite aircraft panel, rib or spa, or a metallic component such as a gas-turbine engine component, a pipeline or a pressure vessel.

BRIEF DESCRIPTION OF THE DRAWINGS

Embodiments of the invention will now be described, by way of example only, with reference to the accompanying drawings, of which.

DESCRIPTION OF EMBODIMENTS

Figure 1:
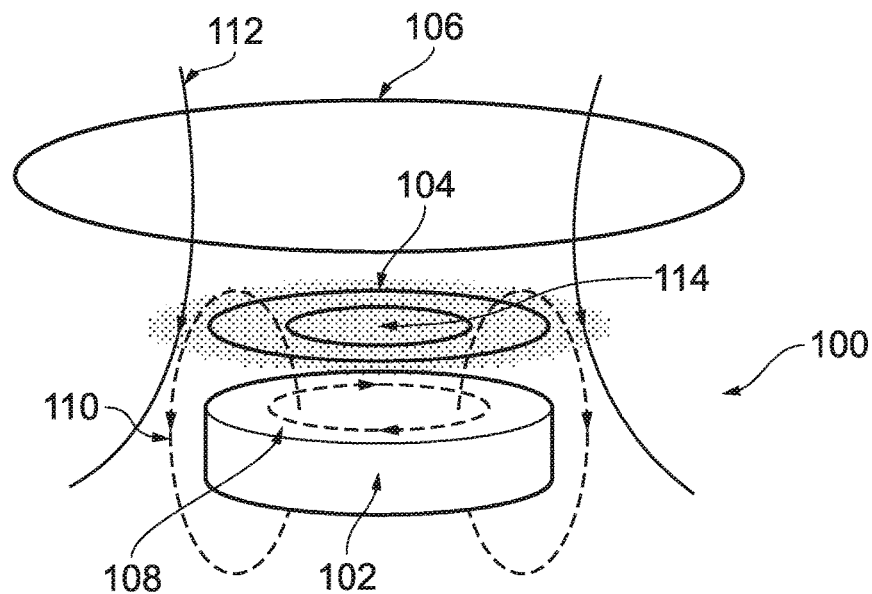
FIG. 1 is a schematic diagram illustrating a problem with wireless NDT sensor design.

FIG. 1 schematically illustrates a problem that the invention seeks to address with a wireless NDT sensor 100 including an electrically conductive transducer element. The NDT sensor 100 includes a piezoelectric transducer 102 and an electromagnetic transducer coil 104 that is electrically coupled to the transducer 102 to enable the transducer 102 to be inductively powered by a remote power source (not shown) via an electromagnetic transmitting coil 106.

To minimise the size of the sensor 100, the present inventors sought to locate the transducer 102 and transducer coil 104 as close together as possible. However, placing the transducer coil 104 directly on top of the transducer 102 leads to a poor inductive coupling between the sensor 100 and remote power source because the transmitting coil 106 generates eddy currents 108 in the conductive electrode of the transducer 102, which in turn generate a magnetic field 110 that cancels out the incident field 112 from the transmitting coil 106, thereby creating an 'uncoupled space' 114 in which the transducer coil 104 is decoupled from the source field.

A known solution to the above-identified problem is to fit a ferrite core between the coil 104 and transducer 102 to control the magnetic flux. See, for example, Greve, Hoon, Yue and Oppenheim, "An Inductively Coupled Lamb Wave Transducer, IEEE sensor journal vol 7 no. 2 2007". However, the present inventions have identified that such a solution results in a bulky, heavy sensor design.

Figure 2A:
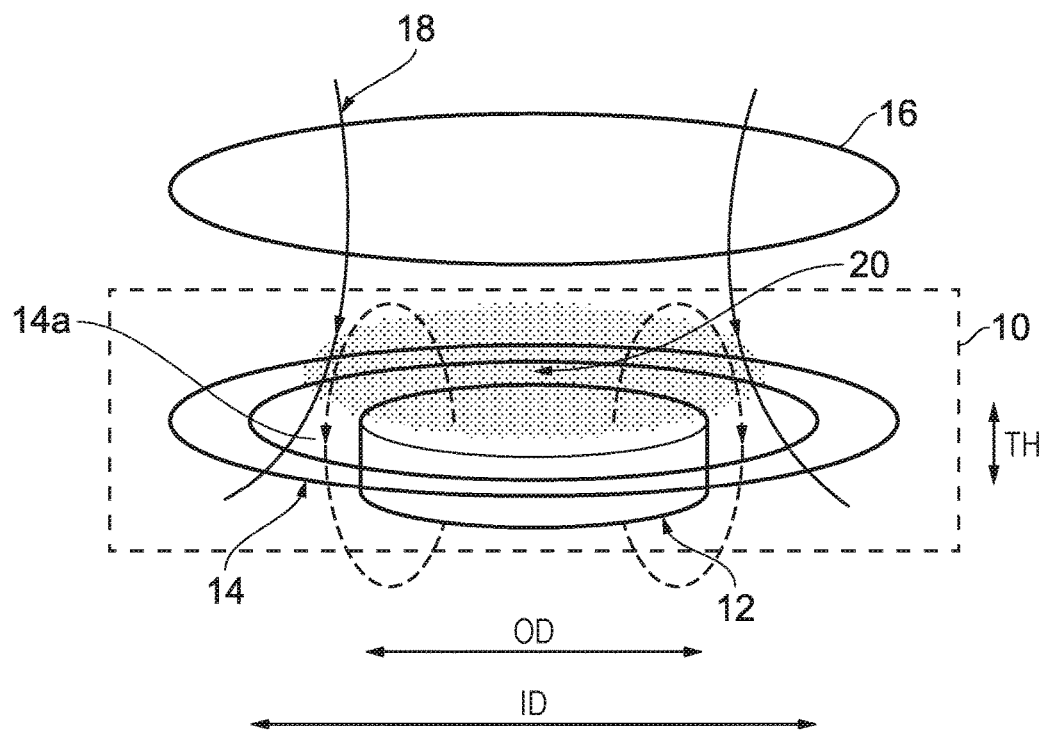
FIGS. 2a, 2b and 2c are schematic diagrams of an NDT sensor according to an embodiment of the invention.
Figure 2B:
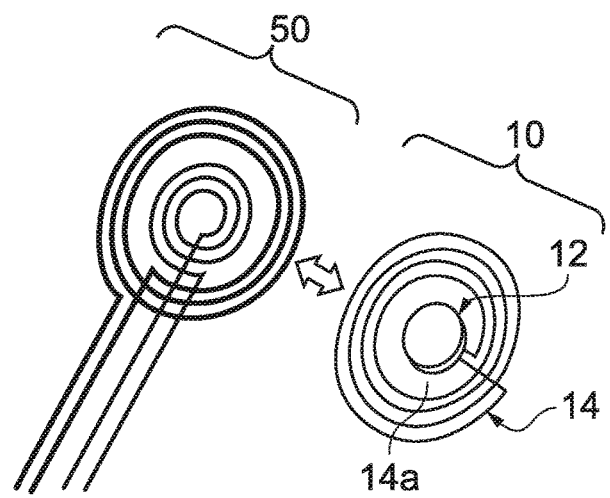
Figure 2C:
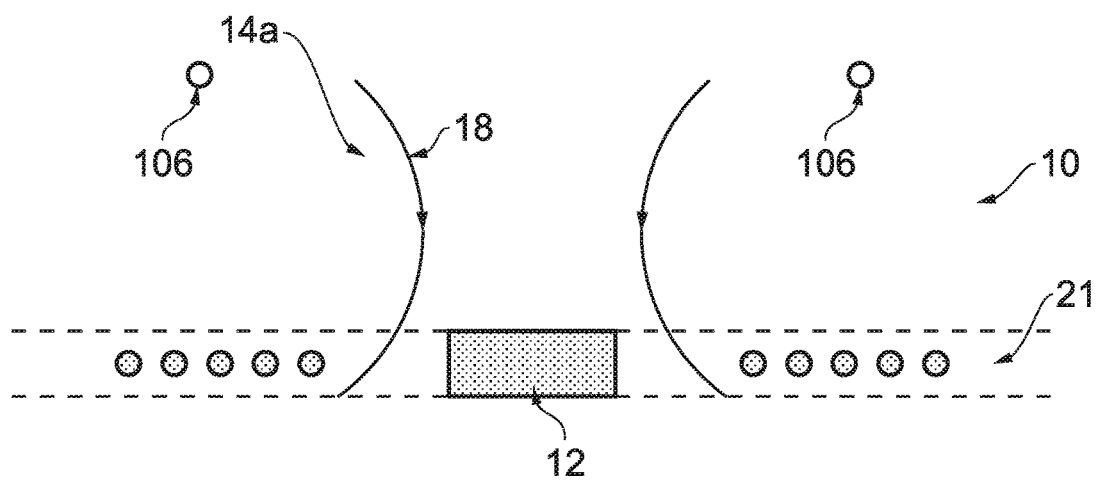

FIGS. 2a, 2b and 2c schematically illustrate a wireless NDT sensor 10 according to an embodiment of the present invention. The sensor 10 includes a transducer 12 and an electrically conductive transducer coil 14 configured to define an open centre or an enclosure 14a and being electrically coupled to the transducer 12 to enable the transducer 12 to be inductively powered by a remote power source (not shown) via a conventional external measurement device 50. As illustrated in FIG. 2a, the transducer coil 14 of the sensor 10 is configured such that the transducer coil 14 can inductively couple to the transmitter coil 16 via magnetic field 18 around the uncoupled space 20.

In the illustrated embodiment the transducer 12 is a piezoelectric disc having a diameter OD of 16 mm and a thickness TH of 0.3 mm to 1 mm depending on the operational frequency of transducer 12. The transducer 12 is formed from NCE51 piezoelectric material supplied by Noliac Group, Kvistgaard, Denmark.

In other embodiments, any suitable transducer may be provided, such as a thermal transducer, a strain gauge, a chemical sensor, an accelerometer, or an RF transducer. As such, certain transducers may not include a conductive electrode and as such will not give rise to the uncoupled space problem referred to above. However, in such embodiments, it is advantageous to provide a transducer coil that is sized to receive the transducer to enable a low profile sensor design. The transducer in embodiments of the invention may have any suitable size and/or shape; for example, a width or diameter of between 2 mm to 30 mm and a thickness of between 0.25 mm and 5 mm.

In the illustrated embodiment the transducer coil 14 is configured as planar coil fabricated on a doubled sided printed circuit board (PCB) (not shown) that surrounds the transducer disc 12. The coil has 38 turns, 19 on each side of the PCB. Although in the illustrated example the transducer coil 14 is printed on a PCB, in other embodiments the coil can be formed by a coiled wire, in some cases mounted on a supporting structure.

The open centre 14a of the transducer coil 14 defines an enclosure of free space that is wider than the transducer 12, meaning that the transducer 12 can be received by and located within the open centre 14a of the transducer coil 14, in the same plane as the transducer 12. In embodiments of the invention, the term 'mounted in the same plane' can mean that a component is mounted so as to be at least partially within, and in some cases completely within, a planar space corresponding to the thickness TH of the transducer 12. This space will be referred to as the 'transducer plane' 21. The inner diameter ID of the transducer coil 14 is in this example larger than the diameter OD of the transducer 12 to provide radial clearance for coupling the coil 14 to the transducer 12. The inner diameter is 24 mm.

In other embodiments, any suitable transducer coil 14 can be provided having one or more distinct internal width dimensions each of which is wider than a corresponding width dimension of the transducer, such that one or more portions of the transducer coil are outside of the decoupled space; for example, an inner diameter ID of between 20 mm to 300 mm. It is preferred that most internal width dimensions of the coil each wider than a corresponding width dimension of the transducer, and even more preferable that the coil enclosure is sized to receive the transducer, preferred embodiments having an internal width that roughly matches the outer width of the transducer.

In the illustrated embodiment, the transducer coil 14 is mounted in the same plane 21 as the transducer 12. This results in a low profile sensor design, suitable for embedding in composite test objects. However, in other embodiments, such as that shown in FIG. 3, the transducer coil 14 can be mounted outside of the transducer plane 21; for example, the transducer coil 14 can be mounted relative to the transducer 12 in a generally coaxial, parallel relationship in which the transducer coil 14 is at least partially outside of the transducer plane 21, and in some cases completely outside, but in close proximity to, the transducer plane 21. In embodiments where the coil 14 is mounted outside of the transducer plane 21, the coil enclosure need not define free space, but could for example be occupied by PCB substrate not defining part of the coil 14.

Once the coil 14 has been connected to the transducer 12, the two components can be encapsulated in an insulating coating; for example, the two components can be encapsulated between sheets of polyimide film bonded together with acrylic adhesive.

Figure 3:
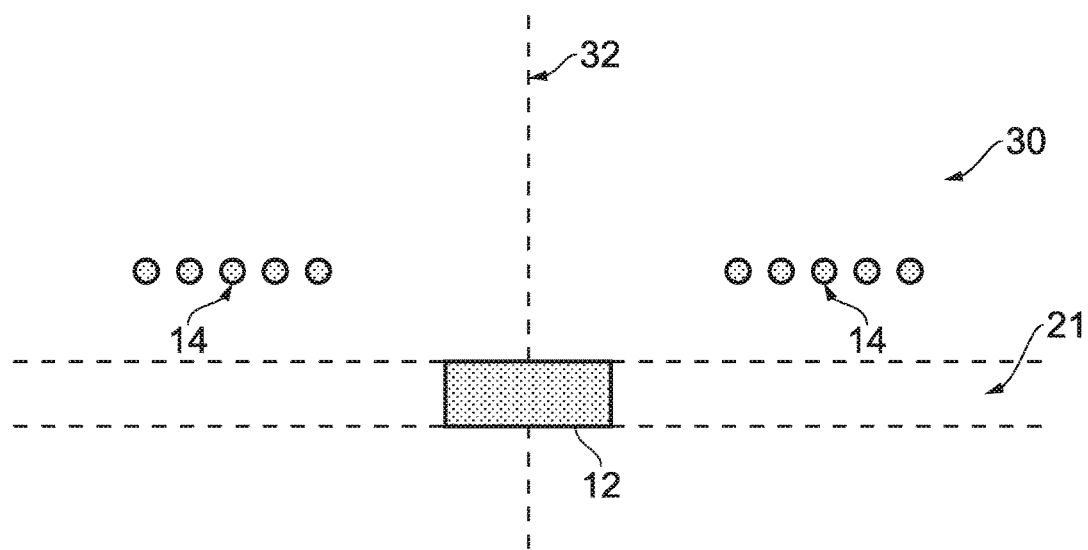
FIG. 3 is a schematic diagram of an NDT sensor according to another embodiment of the invention.

FIG. 3 schematically illustrates, in cross section, a wireless NDT sensor 30 according to an alternative embodiment. In the embodiment shown in FIG. 3, the centre of the transducer coil 14 and the centre of the transducer 12 are axially aligned along an axis 32, with the transducer coil 14 mounted outside of the transducer plane 21. Any suitable support (not shown) may be provided to mount the coil 14, such as a frame formed from a plastics material.

Figure 4:
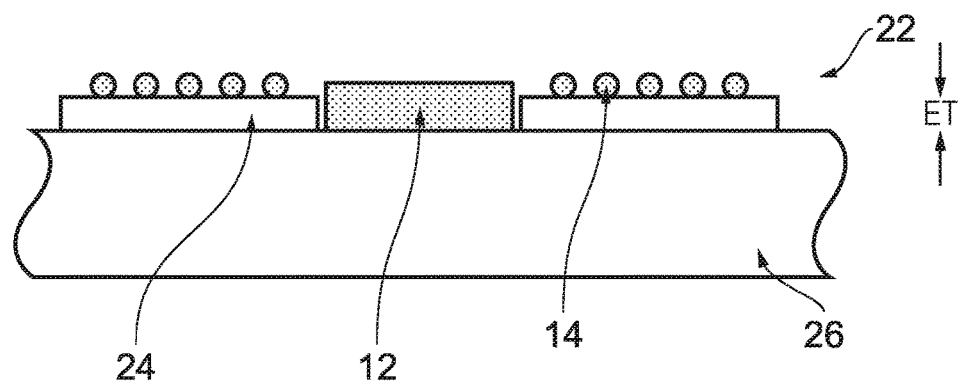
FIG. 4 is a schematic diagram of an NDT sensor according to another embodiment of the invention.

FIG. 4 schematically illustrates, in cross section, a wireless NDT sensor 22 according to another embodiment of the present invention. This embodiment aims to address a problem associated with integrating a wireless NDT sensor on a metallic structure 26. The sensor 22 is similar to the sensor 10 described with reference to FIGS. 2a, 2b and 2c and for brevity only the differences will be described here.

When a wireless NDT sensor is mounted on a metallic structure 26, the transmitting coil (not shown) induces eddy currents at the surface of the metallic structure 26. The eddy currents cause a magnetic field to be generated around the transducer within the transducer plane. The generated magnetic field can adversely affect the inductive coupling between the transmitter coil and transducer coil 14, if the transducer coil 14 is mounted within the transducer plane in close proximity to the metallic structure.

The illustrated embodiment includes a layer of electromagnetic interference (EMI) absorber 24 provided on the reverse side of the coil 14 with respect of the transmitter coil which absorbs incident energy from the transmitter coil so as to inhibit eddy current formation in the metallic structure 26.

The layer of EMI absorber 24 is of a similar size and shape to the coil 14 and is situated within the transducer plane and arranged so as to be generally parallel with respect thereto. However, any suitable arrangement may be provided in which the EMI absorber absorbs incident energy from the transmitter coil so as to inhibit eddy current formation in the metallic structure 26. The EMI absorber 24 enables the transducer coil 14 to be mounted in the transducer plane for an NDT sensor 22 arranged to be applied to metallic structures, providing a low profile, light weight NDT sensor 22.

The EMI material from 24 is formed from CA19 material supplied from Laird Technology, Missouri, USA. In other embodiments, any suitable EMI absorber material may be provided, such as MG series EMI absorber sheet supplied from Intermark, California, USA and AB series EMI absorber supplied from 3M, Minnesota, USA. The EMI layer can have any suitable thickness ET, such as 0.2 to 0.5 mm. The thickness may depend upon the operational frequency of the energising waves.

The EMI absorber can be flexible; for example for example CA19 material supplied from Laird Technology, Missouri, USA. This enables the sensor to be applied to curved structures such as metallic pipes, or integrated into other curved test objects. It is of course preferred that in such embodiments the transducer coil is also flexible.

Wireless NDT sensors according to embodiments of the invention can be embedded or otherwise integrated in a variety of test objects to enable properties of the test object to be evaluated in a quick and simple manner, with excellent test energy coupling and sensor longevity. Moreover, the sensors can be more compact, lighter weight and simpler in design than known wireless integrated NDT sensors.

Although the invention has been described above with reference to one or more preferred embodiments, it will be appreciated that various changes or modifications may be made without departing from the scope of the invention as defined in the appended claims. The word "comprising" can mean "including" or "consisting of" and therefore does not exclude the presence of elements or steps other than those listed in any claim or the specification as a whole. The mere fact that certain measures are recited in mutually different dependent claims does not indicate that a combination of these measures cannot be used to advantage.

The invention claimed is:

1. A wireless sensor suitable for non-destructive testing of a test object, the sensor comprising:
   a transducer; and
   an electrically conductive planar transducer coil arranged in a generally parallel relationship to an upper surface of the transducer and transversely spaced apart therefrom in a range from zero to no more than five times a thickness of the transducer, the transducer coil configured to define an enclosure and being electrically coupled to the transducer to enable the transducer to be inductively operated by a remote device,
   wherein the enclosure defined by the transducer coil has an internal width dimension that is wider than a corresponding width dimension of the transducer and a center of the transducer coil is axially aligned with a center of the transducer.

2. A wireless sensor according to claim 1, wherein the enclosure defined by the transducer coil has a plurality of distinct internal width dimensions each of which is wider than a corresponding width dimension of the transducer.

3. A wireless sensor according to claim 2, wherein the enclosure defined by the transducer coil is sized to receive the transducer.

4. A wireless sensor according to claim 3, wherein the transducer coil is mounted coplanar with the transducer, with transducer located within the enclosure defined by the transducer coil.

5. A wireless sensor according to claim 1, wherein the transducer coil is mounted relative to the transducer in a generally coaxial, parallel relationship in which the transducer coil is spaced from the transducer by no more than five times the thickness of the transducer.

6. A wireless sensor according to claim 1, wherein the coil has one or more distinct inner width dimensions each of which is each between 1.01 and 20 times the corresponding outer width dimension of the transducer.

7. A wireless sensor according to claim 1, wherein the coil has one or more distinct inner width dimensions each of which is at least 1.1 times the corresponding outer width dimension of the transducer.

8. A wireless sensor according to claim 6, wherein an inner width dimension of the coil is a diameter and the corresponding outer width dimension of the transducer is a diameter.

9. A wireless sensor according to claim 1 including a layer of electromagnetic interference (EMI) absorber provided between the transducer coil and a coupling face of the sensor, the coupling face being arranged to be coupled to the test object.

10. A wireless sensor according to claim 9, wherein the layer of EMI absorber is thinner than the transducer.

11. A wireless sensor according to claim 9, wherein the EMI absorber is formed from a flexible material.

12. A wireless sensor according to claim 1, wherein the transducer coil is formed from a flexible material.

13. A wireless sensor according to claim 1, wherein the transducer comprises one of a thermal transducer, an ultrasound transducer, a strain gauge, an accelerometer, and an electromagnetic transducer.

14. A wireless sensor according to claim 1, wherein the coil is arranged as a planar coil.

15. A test object including one or more wireless sensors according to claim 1 coupled to the test object.

16. A test object according to claim 15 comprising a composite or metallic component.

17. A wireless sensor according to claim 1, wherein a layer of electromagnetic interference (EMI) absorber is provided between the transducer coil and a coupling face of the sensor, the coupling face being arranged to be coupled to the test object, and wherein the layer of EMI absorber comprises a polymer containing metallic filler particles.

18. A wireless sensor according to claim 1, wherein the transducer coil and transducer are positioned to reduce cancellation of an incident magnetic field by an induced magnetic field without using any ferrite core.

* * * * *